United States Patent
Jordan et al.

(10) Patent No.: US 6,177,612 B1
(45) Date of Patent: Jan. 23, 2001

(54) MATRIX ATTACHMENT REGIONS

(75) Inventors: Mark Carlyle Jordan; Christof Rampitsch; Marie Sylvie Jacqueline Cloutier, all of Winnipeg (CA)

(73) Assignee: Her Majesty the Queen in right of Canada, as represented by the Department of Agriculture and Agri-Food Canada, Lethbridge (CA)

( * ) Notice: Under 35 U.S.C. 154(b), the term of this patent shall be extended for 0 days.

(21) Appl. No.: 09/553,794

(22) Filed: Apr. 21, 2000

Related U.S. Application Data (63) Continuation-in-part of application No. 09/127,110, filed on Jul. 31, 1998.

(51) Int. Cl.[7] .............................. C12N 15/05; C12N 15/82

(52) U.S. Cl. ...................... 800/278; 435/320.1; 435/468; 435/410; 435/430; 800/295; 800/298; 536/23.1; 536/23.6; 536/24.1

(58) Field of Search ................................ 435/320.1, 468, 435/410, 430; 800/278, 295, 298; 536/23.1, 24.1, 23.6

(56) References Cited

U.S. PATENT DOCUMENTS 5,773,695    6/1998    Thompson et al. ................... 800/293

FOREIGN PATENT DOCUMENTS 2239259    1/2000   (CA) .

OTHER PUBLICATIONS

Rampitsch and Jordan (1998) "An Endosperm–Specific Promoter in Wheat (*Triticum aestifum* L.) Is Adjacent to a Matrix Attachment Region" Hot Topics Abstract Book from 1998 Congress on In Vitro Biology. May 30–Jun. 3, 1998. Las Vegas, Nevada, USA. p. 10.

Rampitsch and Jordan (1998) "An Endosperm–Specific Promoter in Wheat (*Triticum aestifum* L.) Is Adjacent to a Matrix Attachment Region" Book of Abstracts from 16th International Cereal Chemistry Conference. May 9–12, 1998. Vienna, Austria. p. 68.

Rampitsch, Jordan and Cloutier. (1997) Characterization of a Potential Matrix Attachment Region Adjacent to a High Molecular Weight Glutenin Gene in Wheat (*Triticum aestivum* L.) Abstract Book for Plant Biology. Aug. 2–6, 1997. Vancouver, British Columbia. *Plant Physiol.* 114(3):182–183.

Vain et al. (1990) "Matrix Attachment Regions Increase Transgene Expression Levels and Stability in Transgenic Rice Plants and Their Progeny" *The Plant Journal* 18(3):233–242.

Nomura, Koji, et al. 1997. Isolation and Characterization of Matrix Associated Region DNA fragments in Rice (*Oryza sativa* L.) Plant Cell Physiol. 38(9):1060–1068.

Christoffers, M.I. and Gustafson, J.P. Jun. 1996. A Matrix Attachment Region is Found Upstream of an –Amylase Gene is Wheat. Genetic Society of Canada. Bulletin No 27(2).

Avramova, Zoya and Bennetzen, Jeffrey L. 1993. Isolation of matrices from maize leaf nuclei: identification of a matrix–binding site adjacent to the Adh 1 gene, Plant Molecular Biology. 22:1135–1143.

Breyne, Peter et al. 1992. Characterization of a Plant Scaffold Attachment Region in a DNA Fragment that normalizes transgene expression in tobacco. The Plant Cell. vol. 4–463–471.

Mlynarova, Ludmila et al. 1995 The MAR–Mediated Reduction in Position Effect can be uncoupled from Copy Number–Dependent Expression in Transgenic Plants. The Plant Cell, vol. 7–599–609.

Allen, George C., et al. 1993 Scaffold Attachment Regions Increase Reporter Gene Expression in Stably Transformed Plant Cells, The Plant Cell, vol. 5–603–613.

Allen, George C., et al. 1996. High–Level Transgene Expression in Plant Cells: Effects of a Strong Scaffold Attachment Region form Tobacco. The Plant Cell. vol. 8–899–913.

Ulker, Bekir et al. 1997. A tobacco matrix attachment region (MAR) reduces gene silencing in tobacco plants transformed by micro–projectile bombardment. Plant Physiology, vol. 114, No. 3, pp306.

van der Geest, Apolonia H.M., et al. 1994. The β–phaseolin gene is flanked by matrix attachment regions. The Plant Journal. vol. 6(3): 413–423.

Hall, Gerald Jr., et al. 1991. Nuclear scaffolds and scaffold–attachment regions in higher plants. Proc. Natl. Acad. Sci. USA vol. 88: 9320–9324.

Shewry, Peter R., et al. 1995, Biotechnology of Breadmaking: Unraveling and Manipulating the Multi–Protein Gluten Complex, Biotechnology vol. 13:1185–1190.

Spiker, Steven et al. 1996. Nuclear Matrix Attachment Regions and Transgene Expression in Plants. Plant Physiol. 110:15–21.

(List continued on next page.)

*Primary Examiner*—David Guzo
(74) *Attorney, Agent, or Firm*—Greenlee Winner and Sullivan, P.C.

(57) ABSTRACT

Matrix attachment regions isolated from the 5' flanking region of endosperm-specific storage protein genes of monocotyledonous plants are provided. An exemplified matrix attachment region is derived from the 5' flanking region of the Bx7 gluten gene of *Triticum aestivum*. Recombinant nucleic acid molecules and plant vectors containing such recombinant nucleic acid molecules include DNA constructs having a promoter, a coding sequence, and a poly(A) addition site, the DNA constructs operably linked to at least one of the matrix attachment regions. Gene expression in transgenic plants, preferably monocotyledonous cereal crop species, is improved by transforming plants with such recombinant nucleic acid molecules.

37 Claims, 1 Drawing Sheet

OTHER PUBLICATIONS

Schöffl, Fritz et al. 1993. An SAR sequence containing 395 bp DNA fragment mediates enhanced, gene–dosage–correlated expression of a chimaeric heat shock gene in transgenic tobacco plants. Transgenic Research. vol. 2:93–100. Accession No. X13927 (Anderson) (Jun. 25, 1996).

Bode et al. (1992) "Biological Significance of Unwinding Capability of Nuclear Matrix–Association DNAs" *Science* 255:195–197.

Gasser et al. (1986) "Cohabitation of Scaffold Binding Regions with Upstream/Enhancer Elements of Three Developmentally Regulated Genes of D. melanogaster" *Cell* 46:521–530.

Tingay, Sonia; et al. (1997) "*Agrobacterium tumefaciens*–mediated barley transformation". The Plant Journal. 11(6):1369–1376.

Breyne, Peter; et al. (1994) "The role of scaffold attachment regions in the structural and functional organization of plant chromatin". Transgenic Research. 3:196–201.

Cheng, Ming; et al. (1997) "Genetic Transformation of Wheat Mediated by *Agrobacterium tumefaciens*". Plant Physiol. 115:971–980.

Figure

SEQUENCE LISTING

```
<160> NUMBER OF SEQ ID NOS: 8

<210> SEQ ID NO 1
<211> LENGTH: 819
<212> TYPE: DNA
<213> ORGANISM: Triticum aestivum

<400> SEQUENCE: 1
atcgacttga tattatggat atttatgtat ttctctacaa atttgatcaa actttaaaag      60
gtttaacttc tcaaaaaaaa aaactaatac accttatatt ttaaaacaga gagagtagtt     120 ttttttttacc caaaccccaa ctgcccagca aagcgcgctc aactcttcta gtctaaataa    180
ctagcatcca ctaacacatt tctcccgaca tgcaagcacg tcacctatga aaatgcccac    240
ctcaatatgc aaccatgcat agaagaaagc tcacctcagc atgcaaacat gcagcataat    300
ttccatttta cttggctatt tatgtttgat aaatatttca caaatataca ataatcaaaa    360
acaataaatt atatgtgttt ttagtttttag ttctcatatc caaatataca tgtttcatac    420
aaccaaatct catttaaata tattgtaaaa tattccggca acaacttgtg ggggccttaa    480
atatattgta aaatattccg gcaacaactt gtggggtaca tctagttaca gtggaatatt    540
agtgatggcg tgaccaagcg ataaggccaa cgagagaaga agtgcgtcgt ctatggaggc    600
cagggaaaga caatggacat gcaaagaggt aggggcaggg aagaaacact tggagatcat    660
agaagaacat aagaggttaa acataggagg gcataatgga caattaaatc tacattaatt    720
gaactcattt gggaagtaaa caaaatccat attctggtgt aaatcaaact atttgacgcg    780
gatttactaa gatcctatgt taattttaga catgactgg                           819

<210> SEQ ID NO 2
<211> LENGTH: 19
<212> TYPE: DNA
<213> ORGANISM: Triticum aestivum

<400> SEQUENCE: 2
gagctctccc atccaattg                                                   19

<210> SEQ ID NO 3
<211> LENGTH: 20
<212> TYPE: DNA
<213> ORGANISM: Triticum aestivum

<400> SEQUENCE: 3
```

```
agaagcttgg cctggatagt                                              20

<210> SEQ ID NO 4
<211> LENGTH: 19
<212> TYPE: DNA
<213> ORGANISM: Triticum aestivum

<400> SEQUENCE: 4
gggtcgatgg tatcaatcc                                               19

<210> SEQ ID NO 5
<211> LENGTH: 19
<212> TYPE: DNA
<213> ORGANISM: Triticum aestivum

<400> SEQUENCE: 5
ggcctggata gtatgaccc                                               19

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence:consensus

<400> SEQUENCE: 6 aataaayaaa                                                         10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence:consensus

<400> SEQUENCE: 7 ttwtwttwtt                                                         10

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence:consensus
<220> FEATURE:
<223> OTHER INFORMATION: n is any one of a, c, g, or t

<400> SEQUENCE: 8
gtnwayattn atnnr                                                   15
```

MATRIX ATTACHMENT REGIONS

CROSS-REFERENCE TO RELATED APPLICATIONS

This application is a continuation-in-part of United States patent application Ser. No. 09/127,110, filed on Jul. 31, 1998, which is incorporated by reference herein in its entirety.

BACKGROUND OF THE INVENTION

1. Field of the Invention

The invention relates to nucleic acid molecules isolated from the 5' flanking region of endosperm-specific storage protein genes of monocotyledonous plants, and which possess nuclear matrix binding activity.

2. Description of the Related Art

In the past fifteen years it has become possible to transfer genes from any organism into a wide range of crop plants including the major monocotyledonous cereal crops wheat, rice, barley, oat and maize. However, even though the introduced genes can be expressed in the transformed crops, the level of expression can be very low. Indeed, Peach and Velten (1991) found that the majority of detectable transformants exhibited very low expression. The variation in expression is due to the influence of the surrounding chromatin at the site of insertion of the transgene (position effects). As a result, large numbers of transgenic plants must be produced in order to be sure of producing a single high-expressing plant. This is not trivial in cereal crops where the transformation efficiency is only 1 to 5%. In addition to expression variability, there is also the possibility that transgene silencing will occur in subsequent generations.

For the purposes of crop improvement, it would be highly beneficial to reduce the numbers of transgenic plants which need to be produced to find a high-expressing plant, and also to ensure that there will be no transgene silencing in subsequent generations.

In eukaryotes, the DNA is folded into chromosomes in the form of loops. These loops are anchored to a proteinaceous nucleoskeleton, known as the nuclear matrix or scaffold, by segments of DNA known as matrix attachment regions ("MAR"s). The DNA loop structure, which allows for the unwinding of DNA to permit access by transcriptional regulatory proteins, has important implications for gene regulation and expression. One function of the loop structure and matrix attachment regions is to insulate genes from the effects of surrounding chromatin, thereby allowing copy number dependent, position independent expression of adjacent genes. For this reason, various studies have investigated the hypothesis that MARs may allow position independent expression of any introduced genes in transgenic plants.

In several studies, the hypothesis was validated, and MARs were found to increase transgene expression, decrease silencing, prevent silencing after crossing or backcrossing to non-transformed plants, normalize expression, and to provide copy number independent expression (Allen et al. (1996); Allen et al. (1993); Ulker et al. (1997); Mlynarova et al. (1995); Breyne et al. (1992)). These studies utilized MARs derived from either animal or tobacco sources.

Recently, MARs from other plant species such as maize and rice have been isolated (Avramova and Bennetzen (1993); Nomura et al.(1997)). The maize MAR was derived from the promoter of an alcohol dehydrogenase gene. The rice MARs were isolated on the basis of functional binding to the nuclear matrix, and their association with any transcribed gene is unknown.

All of the MARs isolated to date have similar features in that: (1) they are AT rich (greater than 60%); (2) they contain motifs such as A-boxes (consensus sequence AATAAA(T/C)AAA—SEQ ID NO: 6, T-boxes (consensus sequence TT(T/A)T(T/A)TT(T/A)TT—SEQ ID NO: 7), ATATTT boxes, and boxes showing homology to DNA topoisomerase II consensus cleavage sites (consensus sequence GTN(A/T)A(T/C)ATTNATNN(G/A)—SEQ ID NO: 8); and (3) they usually have a length of about 300 to 500 nucleotides (see e.g. Breyne et al. (1992)). None of the mentioned motifs are universal, however, and different MARs do not have extensive homology, nor are there strictly conserved DNA elements. Specific MAR DNA sequences are therefore species specific and differ in their ability to bind the nuclear matrix. Each putative MAR must therefore be investigated by functional assays.

Given the low transformation efficiency in cereal crop plants, MARs functional in cereal crop plants to increase transgene expression, decrease silencing, prevent silencing after crossing or backcrossing to non-transformed plants, normalize expression, and to provide copy number independent expression, would be very useful. The species-specificity of MARs limits the utility of the known rice and maize MARs for improving transgene expression in monocotyledonous cereal crops such as wheat (*Triticum aestivum*). Thus, there is an ongoing need for MARs functional in cereal crop plants.

SUMMARY OF THE INVENTION

The present invention provides a DNA sequence, designated "MAR Bx7", isolated from a region adjacent to a wheat storage protein promoter. The DNA sequence, which is depicted in SEQ ID NO: 1, has features characteristic of MARs in that it is AT rich (63%), and contains motifs homologous to the DNA topoisomerase II consensus sequence (position 709), T-box (position 118) and AATATATTT motif (position 437). Proof that this sequence acts as a matrix attachment region was provided by a functional test of binding to the nuclear matrix. The sequence binds the nuclear matrix and binds more strongly than a previously isolated MAR from maize. The sequence has also been demonstrated to have no deleterious effect when placed adjacent to a heterologous promoter, indicating its utility in enhancing and stabilizing transgene expression. Therefore, in one aspect, the invention provides an isolated nucleic acid molecule comprising the nucleic acid sequence depicted in SEQ ID NO: 1.

As stated above, MAR Bx7 was isolated from the 5' flanking region of a wheat storage protein gene, specifically the Bx7 storage protein gene from *T. aestivum* variety Glenlea. In the developing endosperm of cereals, storage proteins are produced which are not found in any other plant part or at any other stage of development. The genes encoding these proteins are very highly expressed, with up to two percent of the seed protein attributable to each gene. The genes are regulated at the transcriptional level, and are very tightly regulated in that they are only expressed in the developing endosperm. The tight regulation and high expression of these endosperm-specific storage protein genes, including the Bx7 storage protein gene, indicates that MAR Bx7 is highly effective at allowing very high expression rates, and would therefore be useful in enhancing the expression of transgenes in transformed plants.

The present invention provides methods by which the exemplified MAR sequence can be used to identify and isolate other MAR sequences from the 5' flanking region of endosperm-specific storage protein genes of monocotyledonous plants. The inventors have identified DNA sequences within the 5' flanking regions of other endosperm-specific storage protein genes that are closely homologous to the nucleotide sequence of MAR Bx7. The invention provides methods whereby these additional putative MAR sequences can be assayed for nuclear matrix binding activity, and for their ability to enhance or stabilize transgene expression in transgenic monocotyledonous plants. Such additional MAR sequences of the invention have a length of at least 300 nucleotides, preferably at least 500 nucleotides. For use in transforming monocotyledonous plants with a transgene, the MAR sequences of the invention are preferably operably linked to at least one DNA construct which includes a plant promoter, a coding sequence for the gene to be expressed in the plant, and a poly(A) addition signal. Preferably, a MAR sequence of the invention is operably linked both upstream and downstream of the DNA construct. However, a single MAR sequence either upstream or downstream of the DNA construct is sufficient to confer the benefit of the presence of the MAR sequence on expression of the transgene. Therefore, in another aspect, the invention provides a recombinant nucleic acid molecule comprising: a matrix attachment region comprising a nucleic acid molecule having a length of at least 300 nucleotides and which possesses nuclear matrix binding activity, said matrix attachment region being obtained from a 5' flanking region of an endosperm-specific storage protein gene of a monocotyledonous plant; and, at least one DNA construct comprising, in the 5' to 3' direction of transcription, a promoter functional in monocotyledonous plants, a coding sequence expressible in monocotyledonous plants, and a poly(A) addition signal, said matrix attachment region being operably linked to said DNA construct, and being heterologous to at least one of said promoter or said expressible coding sequence.

The invention further extends to plant vectors containing such recombinant nucleic acid molecules, the plant vectors being useful for transforming monocotyledonous crop plants with a foreign gene.

MARs of the invention can be used to enhance transgene expression, provide copy number independent expression and increase stability of transgenes over subsequent generations. The MARs of the invention can be used to flank any promoter/gene combination and inserted into any plant species, preferably monocotyledonous cereal species such as wheat, barley, oat, rice and maize. The invention therefore further extends to recombinant monocotyledonous plants containing stably integrated into their genomes a recombinant nucleic acid molecule as described above.

The invention further extends to methods for improving gene expression in monocotyledonous plants. Broadly stated, such a method comprises the steps of: transforming monocotyledonous plant cells with the above-mentioned recombinant nucleic acid molecule; and, regenerating differentiated transformed plants from said transformed plant cells.

BRIEF DESCRIPTION OF THE DRAWINGS

The FIGURE is a map of plasmid pEM:SP72:EM, which contains MAR Bx7, and which is useful for enhancing the stability and expression of a transgene in a monocotyledonous plant.

DETAILED DESCRIPTION OF THE INVENTION

Figure 1:
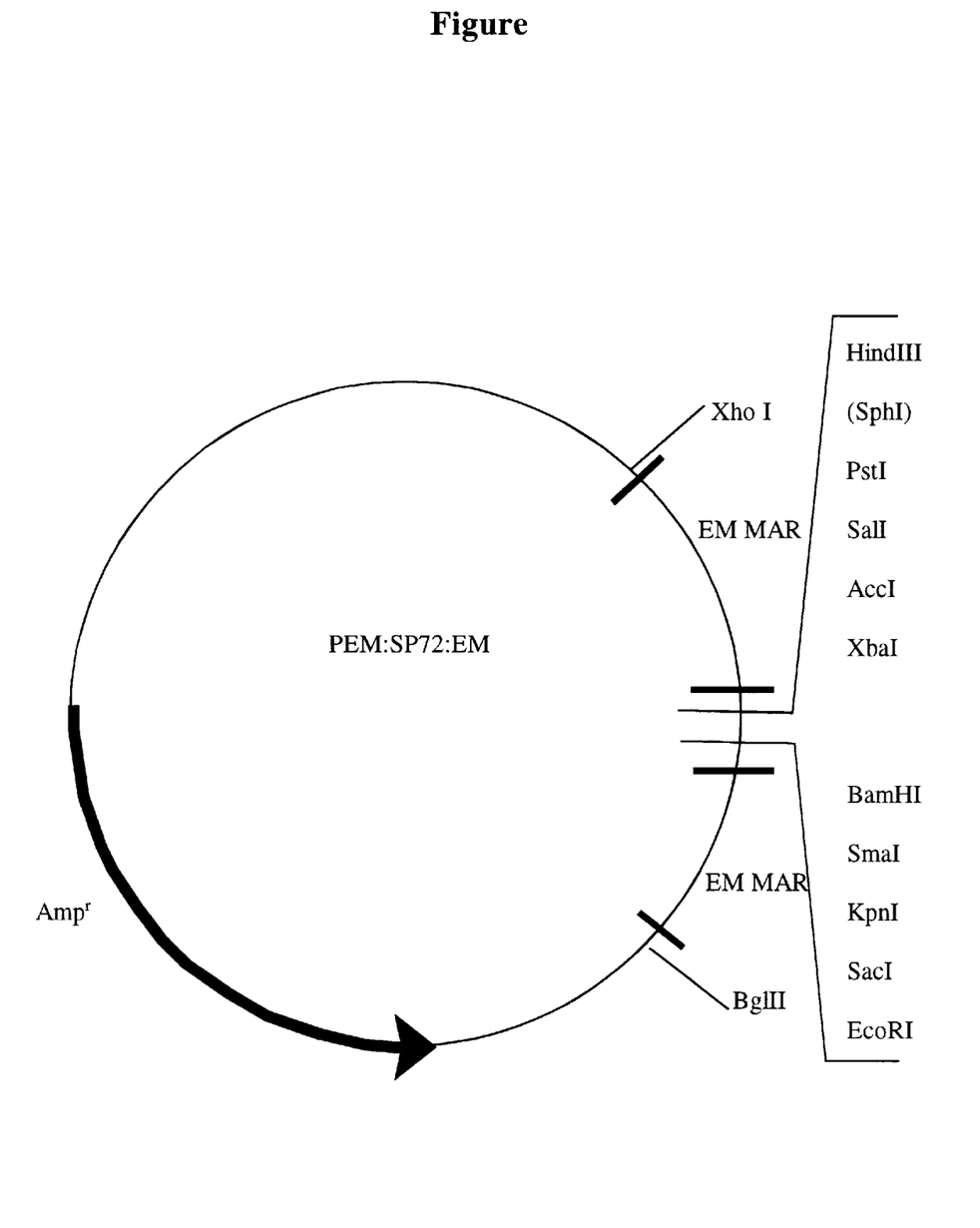

In order to provide a clear and consistent understanding of the specification and claims, including the scope to be given to such terms, the following definitions are provided.

"Coding sequence" means the part of a gene which codes for the amino acid sequence of a protein, or for a functional RNA such as a tRNA or rRNA.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

"Conditions of moderate stringency" means nucleotide sequence hybridization conditions involving washing first in 2×sodium phosphate-ethylenediaminetetracetic acid ("SSPE"), 0.1% sodium dodecyl sulfate ("SDS") at room temperature for 10 minutes followed by washing in 1×SSPE, 0.1% SDS at 65° C. for 15 minutes using Hybond N+ membranes (Amersham Pharmacia, Baie D'Urfe, Quebec, Canada).

A "control" or a "control plant" in an experiment to determine whether the presence of a MAR improves the expression of a transgene, is a plant that has been transformed with an expression cassette comprising a promoter, a coding sequence of interest, and a poly(A) addition site, but which is not operably linked to a MAR. Expression of the coding sequence by the control plant can be compared to that of a plant tranformed with the same expression cassette flanked by MARs, in order to assess the effect of the presence of the MARs. For instance, in the transient expression experiments described in Example 1 herein, the plants tranformed with pAct1d are control plants.

"Downstream" means on the 3' side of any site in DNA or RNA.

"Endosperm-specific storage protein" means a storage protein which is deposited in the developing starchy endosperm of grains. Their biological role is to provide a store of amino acids for germination. The major endosperm-specific storage proteins in wheat are the gluten proteins. Wheat gluten proteins, and the major endosperm-specific storage proteins of most other cereals, are characterized by their insolubility in water or aqueous solutions of salts, but solubility in mixtures of alcohols and water.

"5' flanking region" means the sequences upstream of the coding part of a eukaryotic gene. This region is not transcribed, but contains sequence elements essential for the control of gene expression such as TATA-boxes, CAAT-boxes, enhancers, and specific binding sites for transcription factors.

Two nucleic acid sequences are "heterologous" to one another if the sequences are derived from separate organisms, whether or not such organisms are of different species, as long as the sequences do not naturally occur together in the same arrangement in the same organism.

"Improved expression" of a transgene operably linked to a MAR relative to that of a transgene not linked to a MAR includes, without limitation, such useful properties as increased transgene expression, decreased silencing resulting from position effects, decreased silencing after crossing or back-crossing to non-transformed plants, normalized expression, and increased copy number independent expression.

"Monocotyledonous plant" means the class of flowering plants characterized by the presence of a single seed leaf (cotyledon) in the embryo.

"Nuclear matrix" means the filamentous mesh-work located between the inner nuclear membrane and heterochromatin, which provides potential attachment sites for chromatin and cytoplasmic intermediate filaments. The nuclei of eukaryotic cells have a double-membrane. The outer membrane forms a continuum with some parts of the endoplasmic reticulum whereas the inner membrane functions in the organization of chromatin. The nuclear matrix is made up of a family of interrelated polypeptides known as the nuclear lamins. The nuclear lamins fall into three major types: the neutral A- and C-lamins, and the acidic B-lamins (molecular weight range from 62–69 kDa). Less frequently occurring lamins belong to the D and E categories. The lamins are structurally related to the intermediary filaments, assemble to 10 nm filaments in vivo, and possess the typical coiled coil-configuration of two intertwined α-helices.

"Nuclear matrix binding activity" means the property of a DNA sequence to bind to isolated nuclear matrices in vitro such that it remains attached to the nuclear matrix after centrifugation and is found in the pellet fraction rather than in the supernatant fraction under assay conditions which disfavour binding of prokaryotic plasmid cloning vector DNA to the nuclear matrix such that the cloning vector DNA is associated substantially with the supernatant fraction after centrifugation.

"Nucleic acid molecule" means a single- or double-stranded linear polynucleotide containing either deoxyribonucleotides or ribonucleotides that are linked by 3'-5'-phosphodiester bonds.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

"Plant" means whole plants, plant parts, and plant cells.

A "plant vector" means a cloning vector that is designed to introduce foreign DNA into a plant's genome and includes a plasmid cloning vehicle specifically constructed so as to achieve efficient transcription of the cloned DNA fragments(s) and translation of the corresponding transcript (s) within a target plant cell. Such vectors may be based on, for example, the Ti-plasmid of *Agrobacterium tumefaciens*, or DNA plant viruses.

"Poly(A) addition signal" means a hexanucleotide consensus sequence close to the 3'-end of most eukaryotic genes transcribed by RNA polymerase II, that precedes the site where a poly(A) tail is added to the processed messenger RNA by some 10–30 bases, and is transcribed into mRNA.

"Promoter" means a cis-acting DNA sequence, generally 80–120 base pairs long and located 5' upstream of the initiation site of a gene, to which RNA polymerase may bind and initiate correct transcription. Eukaryotic promoters differ for the different DNA-dependent RNA polymerases. RNA polymerase II, which transcribes structural genes, transcribes a multitude of genes from very different promoters, which have specific sequences in common (e.g. the TATA box at about position −25 and the CAAT box at about position −90).

A "recombinant nucleic acid molecule", for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

"Upstream" means on the 5' side of any site in DNA or RNA.

The first step in obtaining an MAR of the present invention is to clone a cereal (wheat, barley, maize, oat, rice) storage gene promoter region. These species are closely related, and all have similarly regulated endosperm specific storage protein genes. The cloning can be accomplished by methods generally known in the art including, for example: generating DNA primers for the polymerase chain reaction ("PCR") using sequences in the Genbank database where many promoter sequences for storage protein genes are catalogued (for example accession numbers X01130, X17637, X03103, X03042), or using the sequence of MAR Bx7; isolation of a cDNA clone for a storage protein gene and using promoter walking (for example using a commercially available kit such as Promoter Finder from Clonetech (Palo Alto, Calif., USA)); or, probing a genomic library using a cDNA probe for a storage protein gene or a probe for a storage protein gene generated by PCR. This list is not exhaustive, and any method which allows the cloning of a promoter for a gene could be used. The DNA sequence isolated is then cloned into a high copy number cloning plasmid (such as pUC19) and sequenced using sequencing technology well known in the art, for example, as described by Sanger et al. (1977).

The DNA sequence is examined, and any DNA sequences of at least 300 nucleotides, and which have greater than 60% AT content and contain at least one motif with homology to a DNA topoisomerase II consensus site, A box, T box or ATATTT box (Breyne et al., (1994)) are selected as candidates for MAR activity.

The DNA sequences must then be tested for their ability to bind the nuclear matrix. Nuclear matrices (also known as nuclear scaffolds) can be isolated from plant species using either a high salt buffer and Dnase I, or using a lithium diiodosalicylate (LIS) method as reviewed by Breyne et al. (1994). The nuclear scaffolds are incubated with in vitro-labelled DNA fragments (for example, using end-labelling with Klenow fragment and alpha-$^{32}$P dCTP (Sambrook et al. (1989)) of the putative MAR as well as a non-MAR control fragment such as a piece of the prokaryotic cloning vector. Appropriate incubation conditions include, for instance, incubating 2 $A_{260}$ units of nuclear scaffolds for 1 hour at 37° C. with 20 ng of in vitro-labelled DNA fragments and 10 μg control DNA in a total of 100 μl of digestion/binding buffer (20 mM Hepes, pH7.4/20 mM Kcl/70 mM NaCl/10 mM $MgCl_2$/1% thiodoglycol/0.2 mM phenylmethylsulfonyl fluoride/aprotinin at 5 μg/ml) (Hall et al. (1991)). The mixture is centrifuged (for example at 2000×g for 10 minutes (Hall et al. (1991)) and the DNA is isolated from the pellet and supernatant fractions (for example by incubation in 50 μl of lysis buffer (1% SDS/proteinase K at 500 μg/ml/20 mM ethylenediamine tetraacetic acid ("EDTA"), pH 8.0/20 mM Tris-Cl, pH 8.0) for 16 hours at 37 degrees C.)). The two fractions are separated by gel electrophoresis on a 1% agarose Tris/acetate/EDTA ("TAE") gel (Sambrook et al., (1989)), and the gel is then dried and subjected to autoradiography using standard techniques as described by Sambrook et al. (1989).

The putative fragment is confirmed as an MAR if the labelled fragment is found in the pellet fraction. Variations in this assay are possible and can be found for example in Hall et al. (1991), Van der Geest (1994); and Avramova and Bennetzen (1993). Other variations still involving isolation of nuclear matrices and evaluation of the ability of the putative MAR fragment to bind to the matrices may be possible. Significant binding over that of appropriate control fragments indicates that the fragment has MAR activity. Control fragments could include DNA sequences which have been shown to not bind the nuclear matrix by previous assays, or could be prokaryotic or prokaryotic cloning plasmid derived sequences which by nature do not bind the nuclear matrix.

In an alternative method, MAR fragments can be obtained by the isolation of nuclear matrices followed by digestion with one or more restriction enzymes. For instance, nuclear matrices equivalent to 20 $A_{260}$ units of nuclei are incubated in 1 ml of binding/digestion buffer (as described above) with 1000 units of restriction enzyme(s) for 3 hours at 37 degrees C. (Hall et al. (1991)). The endogenous DNA fragments which remain attached to the nuclear matrices are recovered (for example by centrifugation at 2000×g for 10 minutes, washing once with digestion/binding buffer, treatment of the pellet fraction with Rnase A at 200 µg/ml followed by proteinase K at 500 µg/ml (Hall et al., (1991)). The resulting DNA fragments are then extracted with phenol/chloroform and precipitated with ethanol, and then cloned into a plasmid cloning vector using standard techniques (Sambrook et al., (1989)). Variations on this method are possible and can be found in, for example, Mirkovitch et al. (1984) and Nomura et al. (1997).

In the exemplified case, MAR Bx7 was isolated from the 5' flanking region (approximately the 2.2 kb region upstream from the transcription initiation site) of the *Triticum aestivum* variety Glenlea Bx7 storage protein gene. The DNA sequence of this MAR is depicted in SEQ ID NO: 1. MAR Bx7 contains features typical of MARs, being AT rich (63%), and containing motifs homologous to the DNA topoisomerase II consensus sequence (position 709), T-box (position 119) and ATATTT motif (position 437). As shown in Table 1, MAR Bx7 (EM820 fragment) had about 5.9 times the nuclear matrix binding activity of a prokaryotic cloning vector control sequence, and about 2.3 times the nuclear matrix binding activity of the known maize Adh1 gene MAR.

Given the variability exhibited in MAR sequences, it will be appreciated that if any sequence changes were made to the exemplified MAR sequence, the sequence would remain functionally identical to the exemplified MAR as long as the sequence still bound the nuclear matrix in an experiment designed to test the ability of a DNA sequence to bind the nuclear matrix (for example by either of the above assays). Changes to the exemplified MAR sequence, including, for example, insertions, deletions or base changes, may be effected through the use of known techniques, such as the use of commercially available mutagenesis kits from Stratagene, La Jolla, Calif., USA, or Clonetech, Palo Alto, Calif., USA). Naturally occurring sequence variations may also be identified. Therefore, all variants of MAR Bx7 which exhibit greater nuclear matrix binding activity than a prokaryotic cloning vector control fragment under equivalent assay conditions shall be understood to fall within the scope and spirit of the invention.

Example 2 herein provides methods for using MAR Bx7 to identify and isolate other MARs from the 5' flanking region of endosperm-specific storage protein genes of monocotyledonous plants. Analysis of sequence homology between MAR Bx7 and the known MARs from cereal crops, being the maize- and rice-derived MARs reported by Avramova et al. (1993) and Nomura et al. (1997) determined that these MARs have at most 60% and 68% homology, respectively, to MAR Bx7 over the region of greatest similarity. This relatively low level of homology is not surprising, as the known rice and maize MARs are not obtained from the 5' flanking regions of endosperm-specific storage protein genes. As further discussed in Example 2 herein, the inventors have analysed the sequences of 5' flanking regions of various endosperm-specific storage protein genes of wheat or *Aegilops tauschii*, a close relative of wheat. Levels of homology between 86–99% were observed over regions of approximately 100–450 base pairs. Given this degree of sequence homology (greater than about 80%), it is expected, based on the observed properties of MAR Bx7, that these 5' flanking regions of endosperm-specific storage protein genes of wheat or *Aegilops tauschii* contain sequences sufficiently similar to MAR Bx7 that they would have similar functional properties, and would bind the nuclear matrix and function as MARs.

As noted above, *Aegilops tauschii* is closely related to wheat. Bread wheat (*Triticum aestivum L.*) is a hexaploid made up of three genomes, designated genomes A, B and D. Each genome was contributed by a diploid progenitor species. Candidate diploid species include *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome (Mujeeb-Kazi (1993)). There are also tetraploid species containing two of the above genomes. These include *Triticum turgidum* and *Triticum durum* (genomes A and B). All of these species are therefore inter-related and, as such, any MAR found on the B genome of *T. aestivum* would also be found in the B genome of diploid and tetraploid species carrying that genome. The same principle would apply to the other genomes.

There is also a high degree of homology between the genomes of other monocotyledonous plant species and *Triticum aestivum*. This homology is known as gene synteny and allows genes from easily manipulated cereal species having comparatively small genomes, such as rye or rice, to be used to clone genes from wheat. Synteny has been observed between wheat, barley and oats (Hermann, G. G. (1996)); wheat and rye (Langridge, P., et al. (1998)); and wheat, rice, and maize (Ahn, S., et al. (1993)). Due to gene synteny, there is a high probability that the 5' flanking regions of endosperm specific storage protein genes of barley, oats, rye, rice, and maize would contain MARs. Wheat, barley and rye are members of the family Triticeae.

Using the methods disclosed in Examples 1 and 2 herein, fragments of the 5' flanking regions of endosperm-specific storage protein genes of monocotyledonous plant species such as wheat, barley, oats, rye, rice and maize can be identified, isolated, and tested for nuclear matrix binding activity and their effect on the expression of coding sequences in plants. Those sequences which have at least 80% homology to MAR Bx7 are particularly preferred candidates form investigation. Any such sequences which exhibit nuclear matrix binding activity, and which do not have a deleterious effect when placed adjacent to a heterologous promoter, shall be understood to be MARs within the scope and spirit of the invention.

As discussed above, MARs are identified by their ability to bind the nuclear matrix, and it is the very property of nuclear matrix binding activity that defines a MAR, rather than any other feature or property. A helpful general discussion of MARs is provided in Spiker et al. (1996). As noted therein, work with MAR sequences is still in its early stages, particularly in plant systems, and much remains to be learned about the mechanism by which MARs affect transgene expression. Nevertheless, a number of studies have shown that MARs (animal, yeast, soybean and tobacco MARs) are useful for increasing transgene expression in plants (Allen et al. (1996); Allen et al.(1993); Mlynarova et al. (1995); Breyne et al.(1992); and Schoffl et al. (1993)).

Decreased silencing of transgenes through the use of MARs has also been demonstrated (Ulker et al. (1997)). These studies have examined the utility of MARs in less than ideal conditions. For instance Mlynarova et al. (1995) achieved increased expression of the GUS (β-glucuronidase) reporter gene in tobacco plants using a chick lysozyme MAR. As discussed earlier, as different MARs do not have extensive homology, nor are there strictly conserved DNA elements, MARs are species specific and differ in their ability to bind the nuclear matrix. It is therefore to be expected that MARs will have greatest utility in increasing transgene expression in organisms closely related to the source of the MAR sequence. This is borne out in the results reported by Spiker et al. (1996) of their earlier work comparing expression of the GUS reporter gene in tobacco using either a heterologous MAR derived from yeast, or a native tobacco MAR. Use of the yeast (heterologous) MAR resulted in a 12-fold increase in transgene expression, whereas use of the tobacco (homologous) MAR resulted in a 60-fold increase in expression of the transgene. As such, it is expected that while MARs of the present invention, obtained from the 5' flanking region endosperm-specific storage protein genes of monocotyledonous plants, may be used in any plant species, they will be particularly effective in increasing transgene expression in the economically important monocotyledonous cereal species.

To employ MARs of the invention to increase or stabilize transgene expression in plants, recombinant nucleic acid molecules are made wherein an expression cassette or cassettes, each comprising a promoter, coding region and terminator (polyadenylation site), is cloned in such a way that it is adjacent to or preferably flanked by an MAR of the invention. In a preferred embodiment, the resulting recombinant nucleic acid molecule is cloned into a high copy number plasmid or a binary plasmid for use in Agrobacterium. Example 4 herein describes the construction and use of such a plasmid. Suitable high copy number cloning plasmids such as pUC19 or pBluescript are well known in the art and are available commercially from such sources as Life Technologies (Gaithersburg, Md., USA) and Stratagene (La Jolla, Calif., USA). Agrobacterium binary plasmids include pBIN19 and pBI101 and can also be obtained commercially from such sources as the American Type Culture Collection (10801 University Boulevard, Manassas, Va., 20110-2209, USA) and Clonetech (Palo Alto, Calif., USA). Methods for the construction of such constructs are known in the art and are described in commonly used laboratory manuals such as Sambrook et al. (1989).

The constructs containing the gene of interest are then stably inserted into the genome of a plant using known genetic transformation protocols including, without limitation, incorporation into protoplasts using polyethylene glycol ("PEG") or electroporation (Datta et al. (1990)), using Agrobacterium as a delivery system (Tingay et al. (1997)), or bombardment using a device such as described in U.S. Pat. No. 5,179,022. Using these methods, fertile regenerated plants can be produced containing the gene of interest adjacent to or flanked by an MAR of the invention. Such plants will exhibit, on average, increased expression and stability of the gene of interest.

The invention is further illustrated by the following non-limiting examples.

EXAMPLE 1
Isolation of a MAR adjacent to the Bx7 storage protein gene from *Triticum aestivum* variety Glenlea Primers for nested polymerase chain reaction ("PCR") amplification were synthesised by Life Technologies (Gaithersberg, Md., USA). Their sequence was compiled from the coding region of the wheat storage protein gene Bx7* (Genbank Accession No. M22209) (Anderson et al. (1989)) and from sequence in the untranslated upstream region of the related Bx17 gene from *T. aestivum* (wheat) L86-69 (derived from cv. Olympic x cv. Gabo) (Reddy et al. (1993)). These were used to amplify the region upstream of Bx7 in *T. aestivum* cv. Glenlea by polymerase chain reaction. The primer sequences were: (outer primers) GAGCTCTCCCATCCAATTG (SEQ ID NO: 2) and AGAAGCTTGGCCTGGATAGT (SEQ ID NO: 3); and (inner primers) GGGTCGATGGTATCAATCC (SEQ ID NO: 4) and GGCCTGGATAGTATGACCC (SEQ ID NO: 5). The first round of PCR used 200 ng purified 'Glenlea' DNA as template and Taq DNA polymerase in 35 cycles of 30 sec at 92° C. (denature), 30 sec at 52° C. (anneal) and 2.5 min at 72° C. (extend) in a thermocycler (Thermolyne Temptronic) using the outer nested primer pair. The second round of PCR was identical to this, but used 0.2 μl of the first round reaction product and the inner nested primers. The resulting 2.2 kb DNA fragment from the second round of PCR was purified by ethanol precipitation and cloned into the EcoRV site of pBluescript SK (obtained from Stratagene, La Jolla, Calif., USA) using TA-cloning (Zhou et al. (1995)).

The cloned DNA insert was sequenced using the commercial sequencing service of the National Research Council of Canada, Plant Biotechnology Institute (Saskatoon, SK, Canada). The sequence was compared to the Bx17 sequence and to the Bx7 sequence. The plasmid carrying the 2.2 kb MAR insert, called pBx7-2.2, was digested separately with EcoRV & MscI and with MscI & SmaI. The resulting fragments, 0.8 and 0.9 kb respectively, were individually subcloned into pBluescript SK using standard practice (Sambrook et al., (1989) and called pEM820 (containing MAR Bx7) and pMSm900, respectively.

To prove that the cloned sequence functions as a MAR, nuclei were isolated from 7-day etiolated 'Glenlea' seedlings using the procedure described by Steinmüller & Appel (1986) as modified by Cockerill & Garrard (1986). 'Glenlea' wheat was grown in the dark on damp vermiculite for 5 days. Etiolated seedlings were harvested, 100 g ground to a powder in liquid nitrogen and the powder resuspended in 250 ml of isolation buffer (20 mM Tris.HCl pH 7.8, 250 mM sucrose, 5 mM $MgCl_2$, 5 mM KCl, 40% (v/v) glycerol, 0.25% (v/v) Triton X-100, 0.1% (v/v) μ-mercaptoethanol, 1 mM phenylmethylsulfonyl fluoride ("PMSF"), 1 μg/ml leupeptin (Boehringer) and 1 μg/ml aprotinin (Boehringer)). The suspension was warmed to 10° C. by stirring, and then filtered through nylon mesh (0.1 mm) and centrifuged at 0° C., 10,000 g for 15 minutes. All subsequent procedures were performed on ice using chilled buffers. The pellet was carefully resuspended in 150 ml isolation buffer, washed and centrifuged as before but at 6000×g. The pellet was washed again with 100 ml isolation buffer and re-centrifuged as above. The final pellet was resuspended in a minimal volume (approximately 5 ml) of 30 mM sodium phosphate pH 7.8, 1.5 M sucrose, 5 mM $MgCl_2$, 1 mM PMSF, and layered onto a 2.5 ml cushion of the same buffer with 2.3 M sucrose. The sample was centrifuged at 24000 rpm in a Beckman SW27Ti rotor for 30 minutes at 4° C.

The supernatant was removed completely and the pellet resuspended in 2 ml digestion buffer (10 mM Tris.HCl pH 7.8, 250 mM sucrose, 10 mM NaCl, 3 mM $MgCl_2$, 1 mM PMSF) washed and re-centrifuged (750 g, 10 minutes, 4° C.). The pellet was resuspended in 2 ml digestion buffer supplemented with 1 mM $CaCl_2$ and 0.1 mg/ml Dnase I (Pharmacia) and incubated at 23° C. for 1 hour. After centrifugation (as above), pellets were resuspended in 5 ml digestion buffer and mixed with an equal volume of ice-cold 4 M NaCl, 10 mM EDTA, 1 mM PMSF, 20 mM Tris.HCl, pH 7.8. After 10 minutes on ice, the sample was centrifuged at 1500 g, 15 minutes at 4° C., and the pellet re-extracted twice with ice-cold 2 M NaCl, 10 mM EDTA, 10 mM Tris.HCl pH 7.4, 1 mM PMSF, 0.25 mg/ml BSA (Sigma Fraction V) and centrifugation at 4500 g, 15 minutes, 4° C. The pellet (of nuclear matrix) was washed with digestion buffer supplemented with 0.25 mg/ml bovine serum albumin ("BSA"). The final pellet was resuspended in the same buffer (1 ml) combined with an equal volume of glycerol and stored at −20° C.

Binding assays were carried out using a modified procedure of Hall et al. (1991). Crude minipreps of clones to be assayed for binding were digested with XbaI/XhoI (pEM820 and pMSm900). A positive control, the MAR associated with the Adh-1 gene of maize cloned into the BamHI/HindIII site of pUC19, was kindly provided by Z. Avramova, Purdue University, IN, USA. This construct, referred to as pBH1.3, was digested with BamHI/HindIII for the binding experiment. Digested plasmids were labelled with [$\alpha^{32}$P]dCTP using the Klenow fragment (Gibco/BRL) to end-fill the digests, and incubated with nuclear matrices corresponding to 1.0 $A_{260}$ unit of nuclei (as characterized on a spectrophotometer as per Hall et al., (1991)), for one hour in the presence of 20 μg unlabelled competitor DNA (pUC19) in a total volume of 100 μl binding buffer (20 mM Tris.HCl pH 7.4, 20 mM KCl, 70 mM NaCl, 5 mM EDTA, 1 mM dithiothreitol, 1 mM PMSF). After incubation, the suspension was centrifuged and the supernatant transferred to a fresh tube. The pellet was washed once with binding buffer and resuspended in extraction buffer (20 mM Tris.HCl pH 7.4, 5 mM EDTA, 1% (w/v) sodium dodecyl sulphate 100 μl (SDS) and 5 μg sheared salmon sperm DNA (Boehringer)). This was vortexed briefly and heated to 80° C. for 15 minutes. An equal volume of phenol was added to the sample which was again vortexed and heated to 80° C. briefly. The sample was then centrifuged at 13,000×g, at room temperature in a microfuge. The aqueous phase was aspirated and to it was added 0.1 volume 1M NaCl. The DNA was precipitated in ethanol (using standard techniques (Sambrook et al., (1989)). The following was loaded onto a 1% Tris/acetate/edta agarose gel (Sambrook et al., (1989)): the entire final pellet of DNA recovered from the nuclear matrices; 10 μl of the unbound DNA (contained in the nuclear matrix supernatant) and 1 μl of the labelled DNA (used in the binding experiment). These were separated for 1 hour at 65 V in TAE. The gel was fixed by immersion in 1% (w/v) hexadecyltrimethylammonium bromide, 50 mM sodium acetate pH 5.5 for 1 hr. The gel was dried between paper towels and autoradiographed using Biomax film (Kodak). The resulting autoradiogram was placed in a Bio-Rad (Hercules, Calif., USA) visual densitometer and the area under the peaks corresponding to the bands was integrated using a Bio-Rad integrator.

The results of the assay showed that 26.4% of the amount of sequence pEM820 in the assay bound to the nuclear matrix and was found in the pellet fraction as compared to 10.3% for pMSm900 and 11.4% for the previously described (Avramova and Bennetzen, (1993)) maize Adh-I MAR (Table 1). The prokaryotic derived plasmid cloning vector control sequences did not bind the matrix (less than 5%) and were found exclusively in the supernatant. This shows that the sequence of the invention does act as a MAR and binds the matrix more strongly (more than twice) than the previously described maize MAR, making for superior utility.

For utility in enhancing and stabilizing expression for any transgene, it must first be proven that MAR Bx7 does not have a deleterious effect when placed adjacent to a heterologous promoter. As MAR Bx7 is derived from a promoter which is active only in the cereal endosperm, it was necessary to prove that MAR Bx7, when placed adjacent to a constitutive promoter, did not alter the normal expression pattern of the promoter by making it endosperm specific. To prove this, a series of transient expression experiments was conducted. Plasmid pACT1d (Ray Wu, Cornell University, NY, USA) carries the rice actin promoter fused to the uidA gene (encoding the β-glucuronidase ("GUS") protein) and the nopaline synthase ("NOS") polyadenylation signal. Two further plasmids were constructed for transient expression experiments. The actin::GUS::NOS cassette from pACT1d was modified by flanking it with either the EcoRV-MscI (EM) (for plasmid pEM.Act) or the MscI-SmaI (MSm) fragment (for plasmid pMSm.Act) of pBx7-2.2. This was done by cloning the MAR fragments (EM or MSm) in tandem into the PvuII and EcoRV sites of pSP72 (obtained from Promega, Madison, Wis., USA) and then inserting the actin::GUS::NOS cassette into the PstI/XbaI sites between the MARs. For transformation, plasmids were grown in *E. coli* DH5α and purified using a Maxi-Prep kit (Promega). Plasmids were coated onto tungsten particles (1 μm, BioRad, Hercules, Calif., USA) using the method described by Knudsen and Müller ((1991). Tissue for bombardment was embryos and leaves. Embryos were dissected from surface-sterilized wheat seeds ('Glenlea') harvested 15 to 25 days after anthesis. These were placed on solid medium (Knudsen and Müller, (1991); Donovan and Lee (1977)); the composition of this medium is: Murashige and Skoog standard ("MS") medium (Murashige and Skoog (1962)) supplemented with 4.038 g/l casein hydrolysate (BDH), 3% (w/v) sucrose, 100 mg/ml inositol, 0.4 mg/ml thiamine and 1% agarose (Gibco/BRL) pH 5.8), and bombarded with plasmid-coated tungsten particles using a biolistic particle gun (Sanford et al. (1987)). The embryos were incubated in the dark for 24 hours before being assayed for GUS activity by the colorimetric GUS assay (Klein et al. (1988)). Leaves were cut into 5 mm strips, surface-sterilized with ethanol, and transferred to solid medium for bombardment followed by GUS assay.

The results were that both the plasmid with the constitutive rice actin promoter only, and the plasmid with the rice actin promoter adjacent to MAR Bx7 were active in both embryos and leaves (Table 2). This proves that MAR Bx7 is independent from the promoter from which it was derived (which is not active in embryos or leaves) and therefore is not deleterious to the expression pattern of other promoters when placed adjacent to them to enhance expression and stability.

EXAMPLE 2

Use of MAR Bx7 to identify and isolate other MARS from the 5' flanking regions of endosperm-specific storage protein genes of monocotyledonous plants As discussed previously, other MAR sequences from cereal crops (maize and rice) have been reported (Avramova et al., (1993); Nomura et al. (1997)). However, these MARs differ significantly from MAR Bx7. The computer software program Align Plus (Scientific and Educational Software) was used to compare the maize and rice sequences to MAR Bx7. The maize sequence is identified as Genbank Accession number X00581 and the rice sequence is identified as Genbank Accession number X95271. In their entirety, these sequences were, respectively, 2% and 1% homologous to MAR Bx7. However, the maize sequence had a region of 495 base pairs that was 60% homologous to a 527 base pair region of MAR Bx7 and the rice MAR has a 225 base pair sequence which is 68% homologous to a 208 base pair region of MAR Bx7. The region of MAR Bx7 having homology to the maize sequence is not the same region which is homologous to the rice sequence (Table 3). This illustrates the differences between MAR sequences even in related plant species. MAR Bx7 has been shown to be a stronger MAR than the maize sequence (Table 1).

Using MAR Bx7 to search other known DNA sequences (using the BLAST algorithm of Altschul et al. (1990)), a number of sequences with stretches of over 100 base pairs with greater than 80% homology are found. These sequences (Table 4) are all of endosperm specific storage protein genes from wheat or close relatives of wheat (*Aegilops tauschii*), where enough sequence data in the promoter region is present to match that of MAR Bx7. Given the high degree of homology of these promoter regions to MAR Bx7, it is likely that the other sequences contain regions capable of binding the nuclear matrix. Any sequence containing a stretch of over 100 base pairs with 80% or greater homology with MAR Bx7 and capable of binding to the nuclear matrix would be considered to be functionally equivalent to MAR Bx7. The primary source of such sequences would be the 5' flanking region of endosperm specific storage protein genes from wheat or its close relatives. These could be cloned using methods generally known in the art including, for example, generating DNA primers for the polymerase chain reaction (PCR) using sequences in the Genbank database where many promoter sequences for storage protein genes are catalogued (for example accession numbers in Table 4) or using the sequence of MAR Bx7; isolation of a cDNA clone for a storage protein gene (using standard cDNA library techniques as in Sambrook et al. (1989) for example) and using promoter walking (for example using a commercially available kit such as Promoter Finder from Clonetech, Palo Alto, Calif., USA); or probing a genomic library using as a probe a DNA sequence derived from the coding region or promoter of a storage protein gene using moderate stringency washing techniques designed to identify sequences having at least 80% homology to the probe (for example first washing in 2×SSPE, 0.1% SDS at room temperature for 10 minutes followed by washing in 1×SSPE, 0.1% SDS at 65 degrees C. for 15 minutes (manufacturers protocol for moderate stringency washing for Hybond N+ membranes (Amersham Pharmacia, Baie D'Urfe, PQ, Canada). Other membrane types may require different conditions, however a high stringency wash should be omitted. These methods are not exclusive and any method which allows the cloning of a promoter for a gene could be used.

EXAMPLE 3

Use of MAR Bx7 to enhance transgene expression and stability in a monocotyledonous plant A plasmid such as pMAR.Act1d.MAR is constructed so that the MAR Bx7 (EM820) sequence flanks both sides of the β-glucuronidase expression cassette (rice actin promoter-GUS gene-NOS polyadenylation site—the expression cassette contained in plasmid pACT1d described in Example 1 herein). Alternatively, a single MAR sequence could be used to flank one side of the expression cassette only. A construct with the expression cassette but lacking the MAR sequence(s) is used as a control.

The plasmids are transformed into *E. coli* as described in Sambrook et al. (1989), and purified using a Maxi-Prep kit (Promega, Madison, Wis., USA). Plasmids are coated onto tungsten or gold particles (BioRad, Hercules, Calif., USA) using the method described by Knudsen and Müller (1991).

Immature wheat embryos (1.0 to 1.5 mm in length) are pre-cultured and transformed with either the plasmid containing the β-glucuronidase expression cassette flanked by the MAR, or the control plasmid, using a method such as that described in U.S. Pat. No. 5,610,042 or U.S. Pat. No. 5,631,152.

The resulting transformed plants are characterized as to their expression levels using, for example, the fluorometric assay for β-glucuronidase as described by Jefferson (1987). Leaf tissue from each of the plants is ground in extraction buffer (50 mM $NaPO_4$ pH 7.0 buffer, 10 mM β-mercaptoethanol, 10 mM disodium EDTA, pH8.0, 0.1% sodium dodecyl sulphate and 0.1% Triton X-100). An aliquot of 1 to 10 μl is added to 50 μl of extraction buffer plus 1 mM MUG (methyl umbeliferone glucuronide) which is pre-warmed to 37 degrees C. The mixture is incubated at 37 degrees C. for 30 to 60 minutes and then stopped by the addition of 25 μl of 1M sodium carbonate. The mixture is then quantified numerically using a fluorometer. The protein content of the plant extract is determined using commercially available protein assays such as those sold by Bio-Rad (Hercules, Calif., USA). In this way, the values for the level of gene expression per mg protein can be determined for each plant. The expression for the plants containing the MAR sequence is compared to the plants lacking the sequence, and those plants exhibiting increased or stabilized gene expression relative to the control plants are selected.

The transformed plants are also crossed to non-transformed plants. The progeny are then analysed for expression as described above. The series of crossing is done over more than one generation. In this way, the degree of silencing of gene expression for the non-MAR containing construct can be compared to the MAR containing construct.

EXAMPLE 4

Plasmid construct for the use of Mar Bx7 to enhance the expression and stability of any transgene in a monocotyledonous plant A plasmid (Mar Bx7-MCS) is constructed so that the MAR Bx7 (EM820) sequence flanks both sides of a multiple cloning site ("MCS"). An MCS is a DNA sequence which contains the recognition sequence for several restriction endonuclease enzymes. These recognition sequences exist nowhere else in the plasmid and are therefore unique to the MCS. Alternatively, a single MAR sequence is used to flank one side of the MCS only.

The plasmid may be a basic cloning vector plasmid used for routine laboratory cloning purposes as described by Sambrook et al. (1989). An example of a basic cloning vector plasmid is pBluescript (Stratagene, La Jolla, Calif., USA). Alternatively, the plasmid may be a binary vector specifically for use in Agrobacterium sp. Such vectors contain left and right border repeats essential for gene transfer using Agrobacterium. An example is pBIN19 (American Type Culture Collection, Manassas, Va., USA).

As shown in the FIGURE, pEM:SP72:EM is a plasmid that was constructed from a basic cloning vector plasmid. The basic cloning vector plasmid pSP72 (Promega, Madison, Wis., USA) was digested with the restriction endonuclease PvuII. The Bx7 MAR EM fragment was digested from the cloned Bx7 promoter with EcoRV and MscI as described in Example 1. The MAR EM fragment was ligated to the PvuII digested plasmid using standard procedures as described by Sambrook et al. (1989). This new plasmid was then digested with EcoRV. Another copy of the MAR EM fragment was ligated to the EcoRV digested plasmid using standard techniques as described by Sambrook et al. (1989). The resulting plasmid was designated pEM:SP72:EM.

A cloned gene of interest is inserted into the MAR Bx7-MCS plasmid in such a way that it is flanked by the MAR Bx7 region(s). This is done by digesting the plasmid containing the gene of interest with restriction endonuclease (s) (as described by Sambrook et al. (1989)) which remove the gene of interest but do not cut within the gene, and are compatible with one or more restriction endonuclease recognition sites in the MCS region of the MAR Bx7-MCS plasmid. The DNA fragment containing the gene of interest is purified away from the plasmid which carried it by procedures well known by those skilled in the art. For instance, the gene of interest may be isolated by gel electrophoresis, followed by cutting out the piece of the gel containing the gene of interest and eluting the DNA as described by Sambrook et al. (1989). Digestion of the MAR Bx7-MCS plasmid with the appropriate enzyme(s) is followed by ligation of the digested plasmid with the DNA of the gene of interest using procedures described by Sambrook et al. (1989) and which are familiar to those skilled in the art.

The resulting plasmid is used to transform a monocotyledonous plant. If the MAR Bx7-MCS plasmid was a basic cloning vector the resulting plasmid may be transformed into E. coli, purified, coated onto gold particles and used for transformation, as described in Example 3. If the MAR Bx7-MCS plasmid was an Agrobacterium binary type plasmid, it may be transformed into Agrobacterium by, for instance, electroporation using electro-competent Agrobacterium cells (Life Technologies Inc, Gaithersburg, Md., USA). The Agrobacterium strain containing the binary plasmid is used to transform a monocotyledonous plant using, for instance, the procedure of Tingay et al. (1997) for barley, or the procedure of Cheng et al. (1997) for wheat.

TABLE 1

Results of binding assay with the two subcloned fragments of the Bx7 2.2 kb promoter fragment (EM820 and Msm900) and the AdhI MAR positive control. Each fragment has its own internal negative control vector fragment. Data is presented for the area under the peaks corresponding to the bands on the autoradiogram after densitometric analysis. Area units are assigned by the integrator.

| Area under peak | vector control-Adh1 | Adh1 fragment | vector control-EM820 | EM820 fragment (MAR Bx7) | vector control-MSm900 | Msm900 fragment |
| --- | --- | --- | --- | --- | --- | --- |
| supernatant | 59975328 | 78028861 | 7465160 | 3351453 | 60897560 | 1859769 |
| pellet | 2213018 | 8917389 | 64511520 | 17037888 | 57563920 | 5936224 |
| % in pellet | 3.7 | 11.4 | 4.5 | 26.4 | 3.1 | 10.3 |

TABLE 2

Results of transient GUS expression in tissues transformed with pAct1d and MAR-flanked actin::GUS::NOS constructs.

| Construct | Embryo | Endosperm | Callus | Leaf |
| --- | --- | --- | --- | --- |
| pAct1d | +++ | ++ | ND | + |
| pEM.Act | +++ | ++ | +++ | + |
| pMSm.Act | +++ | ++ | ND | + |
| Unshot | − | − | − | − |

ND = not determined
+++ = 20% of tissue had >10 spots per tissue piece and <20% had no spots
++ = approximately 50% had no spots per tissue piece and <20% had >10 spots
+ = at least one spot per construct per tissue
− = no spots

TABLE 3

Homology of MAR Bx7 with other disclosed cereal species MAR regions.

| Accession Number and region of homology (base pairs) | Region of Homology in MAR Bx7 (base pairs) | % homology |
| --- | --- | --- |
| X00581 (169–664) | 6–553 | 60 |
| X95271 (18–243) | 559–807 | 68 |

TABLE 4

BLAST similarity search using MAR Bx7 as query sequence. All accessions are wheat or Aegilops endosperm specific storage protein gene promoter regions.

| Accession Number | Length of Homologous Region (Base pairs) | % Homology |
| --- | --- | --- |
| X13927 | 343 | 99 |
| X13927 | 458 | 92 |
| M22208 | 174 | 94 |
| X03042 | 104 | 86 |

REFERENCES

Ahn, S., et al. Mol. Gen. Genet., 241, 483–490 (1993).
Allen et al., Plant Cell, 5, 603–613, (1993).
Allen et al., Plant Cell, 8, 899–913, (1996).
Altschul et al., J. Mol. Biol., 215, 403–410, (1990).
Anderson, O. D., Greene, F. C., Theor. Appl. Genet., 77, 689–700, (1989).
Avramova and Bennetzen, Pl. Mol. Biol., 22, 1135–1143, (1993).
Breyne et al., Plant Cell, 4, 463–471, (1992).
Breyne et al., Transgenic Res., 3, 195–202, (1994).
Cheng et al., Plant Physiol., 115, 971–980, (1997).
Cockerill & Garrard, Cell, 4, 273–382, (1986).
Datta et al., Biotechnology, 8, 736–740, (1990).
Donovan and Lee, Plant Sci. Lett., 9, 107–113, (1977).
Jefferson, Pl. Mol. Biol. Reporter, 5, 387–405, (1987).
Hall et al. PNAS, USA, 88, 9320–9324, (1991).
Hermann, G. G., et al., Symp. Soc. Exp. Biol., 50, 25–30, (1996).
Klein et al., PNAS, USA, 85, 4305–4309, (1988).
Knudsen and Muller, Planta, 185, 330–336, (1991).
Langridge, P., et al. Mol. Gen. Genet., 257, 568–575, (1998).
Mirkovitch et al., Cell, 39, 223–232, (1984).
Mlynarova et al., Plant Cell, 7, 599–609, (1995).
Mujeeb-Kazi, A. In Biodiversity and Wheat Improvement, A. B. Damania (editor). 1993. A Wiley-Sayce Publication, pp. 95–102.

Murashige and Skoog, Physiol. Plant., 15, 474–497, (1962).
Nomura et al., Plant Cell Physiol., 38, 1060–1068, (1997).
Peach and Velten, Plant Mol. Biol., 17, 49–60 (1991).
Reddy, P., Appels, R., Theor. Appl. Genet., 85, 616–624, (1993).
Sambrook et al., Molecular Cloning, Cold Spring Harbor Press, (1989).
Sanford et al., Particulate Sci. Technol., 5, 27–37, (1987).
Sanger, F., et al. Proc. Natl. Acad. Sci. USA, 74,563–568, (1977).
Schoffl et al., Transgenic Res. 2, 93–100, (1993).
Spiker et al., Plant Physiol., 110, 15–21, (1996).
Steinmüller & Appel, Plant Molecular Biology, 7, 87–94 (1986).
Tingay et al., Plant J., 11(6), 1369–1376, (1997).
Ulker et al., Plant Physiol. 114, 306, (1997).
Van der Geest, Plant J., 6, 413–423, (1994).
Zhou et al., Biotechniques, 19, 34–35, (1995).

All publications mentioned in this specification are indicative of the level of skill in the art to which this invention pertains. To the extent that they are consistent herewith, all publications are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. A recombinant nucleic acid molecule comprising:
    (a) a matrix attachment region comprising a nucleic acid molecule having a length of at least 300 nucleotides and which possesses nuclear matrix binding activity, said matrix attachment region being obtained from a 5' flanking region of an endosperm-specific storage protein gene of a monocotyledonous plant; and,
    (b) at least one DNA construct comprising, in the 5' to 3' direction of transcription, a promoter functional in monocotyledonous plants, a coding sequence expressible in monocotyledonous plants, and a poly(A) addition signal,
said matrix attachment region being operably linked to said DNA construct, and being heterologous to at least one of said promoter or said expressible coding sequence.

2. A recombinant nucleic acid molecule as set forth in claim 1, wherein said monocotyledonous plant is of the family Triticeae.

3. A recombinant nucleic acid molecule as set forth in claim 1, wherein said monocotyledonous plant is of the species *Triticum aestivum*.

4. A recombinant nucleic acid molecule as set forth in claim 1, wherein said matrix attachment region comprises a nucleic acid molecule, the complement of which hybridizes under conditions of moderate stringency with a nucleotide sequence comprising at least 100 continuous nucleotides of the sequence depicted in SEQ ID NO: 1.

5. A recombinant nucleic acid molecule as set forth in claim 1, wherein said matrix attachment region:
    (a) possesses at least five times the nuclear matrix binding activity of a control sequence consisting of prokaryotic plasmid cloning vector DNA;
    (b) has an A-T content of at least 60%; and,
    (c) includes at least one of a DNA topoisomerase II consensus sequence, a T-box, or an ATATTT motif.

6. A recombinant nucleic acid molecule as set forth in claim 1, wherein said matrix attachment region comprises the nucleic acid sequence depicted in SEQ ID NO: 1.

7. A recombinant nucleic acid molecule as set forth in claim 1, wherein said matrix attachment region is located upstream of said at least one DNA construct.

8. A recombinant nucleic acid molecule as set forth in claim 1, wherein said matrix attachment region is located downstream of said at least one DNA construct.

9. A recombinant nucleic acid molecule as set forth in claim 1, wherein said matrix attachment region is located both upstream and downstream of said at least one DNA construct.

10. An isolated nucleic acid molecule comprising the nucleic acid sequence depicted in SEQ ID NO: 1.

11. A plant vector comprising a recombinant nucleic acid molecule according to claim 1.

12. A plant vector comprising a recombinant nucleic acid molecule according to claim 2.

13. A plant vector comprising a recombinant nucleic acid molecule according to claim 3.

14. A plant vector comprising a recombinant nucleic acid molecule according to claim 4.

15. A plant vector comprising a recombinant nucleic acid molecule according to claim 5.

16. A plant vector comprising a recombinant nucleic acid molecule according to claim 6.

17. A plant vector comprising a recombinant nucleic acid molecule according to claim 7.

18. A plant vector comprising a recombinant nucleic acid molecule according to claim 8.

19. A plant vector comprising a recombinant nucleic acid molecule according to claim 9.

20. A transgenic monocotyledonous plant containing stably integrated into its genome a recombinant nucleic acid molecule according to claim 1.

21. A transgenic monocotyledonous plant containing stably integrated into its genome a recombinant nucleic acid molecule according to claim 2.

22. A transgenic monocotyledonous plant containing stably integrated into its genome a recombinant nucleic acid molecule according to claim 3.

23. A transgenic monocotyledonous plant containing stably integrated into its genome a recombinant nucleic acid molecule according to claim 4.

24. A transgenic monocotyledonous plant containing stably integrated into its genome a recombinant nucleic acid molecule according to claim 5.

25. A transgenic monocotyledonous plant containing stably integrated into its genome a recombinant nucleic acid molecule according to claim 6.

26. A transgenic monocotyledonous plant containing stably integrated into its genome a recombinant nucleic acid molecule according to claim 7.

27. A transgenic monocotyledonous plant containing stably integrated into its genome a recombinant nucleic acid molecule according to claim 8.

28. A transgenic monocotyledonous plant containing stably integrated into its genome a recombinant nucleic acid molecule according to claim 9.

29. A method for providing improved gene expression in a transgenic monocotyledonous plant, comprising the steps of:
    (a) transforming monocotyledonous plant cells with a recombinant nucleic acid molecule according to claim 1; and,
    (b) regenerating differentiated transformed plants from said transformed plant cells.

30. A method for providing improved gene expression in a transgenic monocotyledonous plant, comprising the steps of:
    (a) transforming monocotyledonous plant cells with a recombinant nucleic acid molecule according to claim 2; and,
    (b) regenerating differentiated transformed plants from said transformed plant cells.

31. A method for providing improved gene expression in a transgenic monocotyledonous plant, comprising the steps of:
    (a) transforming monocotyledonous plant cells with a recombinant nucleic acid molecule according to claim 3; and,
    (b) regenerating differentiated transformed plants from said transformed plant cells.

32. A method for providing improved gene expression in a transgenic monocotyledonous plant, comprising the steps of:
    (a) transforming monocotyledonous plant cells with a recombinant nucleic acid molecule according to claim 4; and,
    (b) regenerating differentiated transformed plants from said transformed plant cells.

33. A method for providing improved gene expression in a transgenic monocotyledonous plant, comprising the steps of:
    (a) transforming monocotyledonous plant cells with a recombinant nucleic acid molecule according to claim 5; and, (b) regenerating differentiated transformed plants from said transformed plant cells.

34. A method for providing improved gene expression in a transgenic monocotyledonous plant, comprising the steps of:
    (a) transforming monocotyledonous plant cells with a recombinant nucleic acid molecule according to claim 6; and,
    (b) regenerating differentiated transformed plants from said transformed plant cells.

35. A method for providing improved gene expression in a transgenic monocotyledonous plant, comprising the steps of:
    (a) transforming monocotyledonous plant cells with a recombinant nucleic acid molecule according to claim 7; and,
    (b) regenerating differentiated transformed plants from said transformed plant cells.

36. A method for providing improved gene expression in a transgenic monocotyledonous plant, comprising the steps of:
    (a) transforming monocotyledonous plant cells with a recombinant nucleic acid molecule according to claim 8; and,
    (b) regenerating differentiated transformed plants from said transformed plant cells.

37. A method for providing improved gene expression in a transgenic monocotyledonous plant, comprising the steps of:
    (a) transforming monocotyledonous plant cells with a recombinant nucleic acid molecule according to claim 9; and,
    (b) regenerating differentiated transformed plants from said transformed plant cells.

* * * * *